(12) United States Patent
Song et al.

(10) Patent No.: US 11,731,919 B2
(45) Date of Patent: Aug. 22, 2023

(54) APPARATUS FOR PREPARING OLIGOMER

(71) Applicant: LG CHEM, LTD., Seoul (KR)

(72) Inventors: Jong Hun Song, Daejeon (KR); Jeong Seok Lee, Daejeon (KR); Hong Min Lee, Daejeon (KR); Moon Sub Hwang, Daejeon (KR); Min Ho Sun, Daejeon (KR); Kyung Seog Youk, Daejeon (KR)

(73) Assignee: LG Chem, Ltd., Seoul (KR)

( * ) Notice: Subject to any disclaimer, the term of this patent is extended or adjusted under 35 U.S.C. 154(b) by 65 days.

(21) Appl. No.: 17/633,874

(22) PCT Filed: Jul. 1, 2021

(86) PCT No.: PCT/KR2021/095071
§ 371 (c)(1),
(2) Date: Feb. 8, 2022

(87) PCT Pub. No.: WO2022/019734
PCT Pub. Date: Jan. 27, 2022

(65) Prior Publication Data
US 2022/0340500 A1 Oct. 27, 2022

(30) Foreign Application Priority Data
Jul. 24, 2020 (KR) .................. 10-2020-0092456

(51) Int. Cl.
*C07C 2/04* (2006.01)
(52) U.S. Cl.
CPC ........... *C07C 2/04* (2013.01); *B01J 2204/005* (2013.01); *B01J 2219/00162* (2013.01); *B01J 2219/00247* (2013.01)

(58) Field of Classification Search
CPC . C07C 2/04; C07C 11/107; B01J 4/001; B01J 19/0006; B01J 2204/005;
(Continued)

(56) References Cited

U.S. PATENT DOCUMENTS 8,658,750 B2 2/2014 Lattner et al.
2005/0113515 A1 5/2005 Sutton et al.
(Continued)

FOREIGN PATENT DOCUMENTS

CN 201372260 Y 12/2009
CN 105363237 A 3/2016
(Continued)

OTHER PUBLICATIONS

Alzaid, et al.(2018). "Impact of Molecular Structure on the Hydrogenation and Oligomerization of Diolefins Over A Ni—Mo—S/γ-Al2O3 Catalyst", Fuel, vol. 221. pp. 206-215.

*Primary Examiner* — Ali Z Fadhel
(74) *Attorney, Agent, or Firm* — Bryan Cave Leighton Paisner LLP (57) ABSTRACT

An apparatus for preparing an oligomer including: a reactor supplied with a monomer stream and a solvent stream to perform an oligomerization reaction; a product discharge line provided on a lower portion of a side surface of the reactor; a washing liquid supply line connected to a first point of the product discharge line; and a washing liquid discharge line extending from a second point of the product discharge line, wherein the product discharge line includes a branch point at which the product discharge line is branched into two or more lines and a junction point at which the respective branched lines are joined, and the product discharge line includes pressure control devices provided in each of the two or more branched lines.

14 Claims, 3 Drawing Sheets

(58) Field of Classification Search
CPC .... B01J 2219/00038; B01J 2219/00162; B01J 2219/00164; B01J 2219/00247
See application file for complete search history.

(56) References Cited

U.S. PATENT DOCUMENTS

| | | | |
|---|---|---|---|
| 2009/0088538 | A1 | 4/2009 | Campman et al. |
| 2009/0203947 | A1* | 8/2009 | Schneider ................. C07C 7/09 422/198 |
| 2013/0144024 | A1* | 6/2013 | Lattner .................... B01J 8/382 585/511 |
| 2018/0179122 | A1* | 6/2018 | Boutrot ................ B01J 19/2465 |
| 2019/0322965 | A1* | 10/2019 | Alqahtani ............... C11D 7/244 |
| 2020/0062672 | A1* | 2/2020 | Weber ...................... C08F 10/00 |
| 2020/0139334 | A1* | 5/2020 | Al-Dughaiter ............ C07C 2/08 |

FOREIGN PATENT DOCUMENTS

| | | |
|---|---|---|
| CN | 108025995 A | 5/2018 |
| CN | 108218661 A | 6/2018 |
| CN | 210085325 U | 2/2020 |
| CN | 210613412 U | 5/2020 |
| JP | 2005-264231 A | 9/2005 |
| JP | 2005264231 A | 9/2005 |
| JP | 2010172793 A | 8/2010 |
| JP | 2018-076257 A | 5/2018 |
| JP | 2018-108983 A | 7/2018 |
| JP | 6685299 B2 | 4/2020 |
| KR | 10-2007-0028576 A | 3/2007 |
| KR | 10-2017-0127982 A | 11/2017 |
| KR | 10-1816097 B1 | 1/2018 |
| KR | 10-2018-0055815 A | 5/2018 |
| KR | 10-2018-0118079 A | 10/2018 |

\* cited by examiner

APPARATUS FOR PREPARING OLIGOMER

CROSS-REFERENCE TO RELATED APPLICATION(S)

This application is a National Phase entry pursuant to 35 U.S.C. § 371 of International Application No. PCT/KR2021/095071, filed on Jul. 1, 2021, and claims the benefit of and priority to Korean Patent Application No. 10-2020-0092456, filed on Jul. 24, 2020 in the Korean Intellectual Property Office, the disclosures of which are incorporated by reference in their entirety for all purposes as if fully set forth herein.

TECHNICAL FIELD

The present invention relates to an apparatus for preparing an oligomer, and more particularly, to an apparatus for preparing an oligomer for preventing a plugging phenomenon in a line (pipe) through which a product is discharged at the time of preparing an oligomer.

BACKGROUND ART

Alpha-olefins are an important material used in comonomers, detergents, lubricants, plasticizers, and the like, and are commercially widely used. Among them, 1-hexene and 1-octene have been widely used as comonomers for controlling a density of polyethylene at the time of preparing linear low-density polyethylene (LLDPE).

The alpha-olefins such as 1-hexene and 1-octene have been typically prepared through an oligomerization reaction of ethylene. The oligomerization reaction of ethylene is performed by an oligomerization reaction (a trimerization reaction or a tetramerization reaction) of ethylene in the presence of a catalyst using ethylene as a reactant, a product produced through the oligomerization reaction includes small amounts of wax and polymer material produced during a catalytic reaction as well as a multi-component hydrocarbon mixture including desired 1-hexene and 1-octene, and these materials are attached to a line through which the product is discharged, causing a plugging phenomenon in which a pipe is plugged.

In a case where plugging occurs in a product discharge line of a reactor, an operation of the reactor should be shut down to wash the product discharge line of the reactor, and thus, there was a problem such as an increase in cost required for a washing process as well as a decrease in production amount due to a decrease in operation time.

DISCLOSURE

Technical Problem

An object of the present invention is to provide an apparatus for preparing an oligomer capable of preventing occurrence of plugging in a line through which a product is discharged in a reactor, further including a line for washing at the time of occurrence of plugging in a product discharge line, and being continuously operated without stopping an operation to solve a problem such as a decrease in production amount and decrease a cost required for a washing process.

Technical Solution

According to an exemplary embodiment of the present invention, there is provided an apparatus for preparing an oligomer, including: a reactor supplied with a monomer stream and a solvent stream to perform an oligomerization reaction; a product discharge line provided on a lower portion of a side surface of the reactor; a washing liquid supply line connected to a first point of the product discharge line; and a washing liquid discharge line extending from a second point of the product discharge line, wherein the product discharge line includes a branch point at which the product discharge line is branched into two or more lines and a junction point at which the respective branched lines are joined, and the product discharge line includes pressure control devices provided in each of the two or more branched lines.

Advantageous Effects

With the apparatus for preparing an oligomer according to the present invention, the product discharge line can be branched into the two or more lines, the pressure control devices can be provided in each of the branched lines to prevent a polymer material from being precipitated from a product discharge stream, and the respective branched lines can be alternately used to extend an operation cycle.

In addition, in the present invention, the washing liquid supply line supplying the washing liquid and the washing liquid discharge line for discharging the washing liquid can be provided in the respective branched lines to easily wash the polymer materials fouled in the pressure control devices provided in the respective branched lines.

Further, in the present invention, lines for washing the respective branched lines while continuously operating the reactor without stopping an operation of the reactor can be provided to solve a problem such as a decrease in a production amount and decrease a cost required for a washing process.

DETAILED DESCRIPTION

Terms and words used in the present specification and claims are not to be construed as a general or dictionary meaning, and are to be construed as meaning and concepts meeting the technical spirit of the present invention based on a principle that the inventors may appropriately define the concepts of terms in order to describe their own inventions in the best mode.

In the present invention, the term 'stream' may refer to a flow of a fluid in a process or refer to a fluid itself flowing in a moving line (pipe). Specifically, the 'stream' may refer to both a fluid itself flowing in a pipe connecting respective devices to each other and a flow of the fluid. In addition, the fluid may include any one or more of a gas, a liquid, and a solid.

Hereinafter, the present invention will be described in more detail with reference to FIGS. 1 to 5 in order to assist in the understanding of the present invention.

According to the present invention, there is provided an apparatus for preparing an oligomer. As the apparatus for preparing an oligomer, there is provided an apparatus for preparing an oligomer including: a reactor 100 supplied with a monomer stream and a solvent stream to perform an oligomerization reaction; a product discharge line 200 provided on a lower portion of a side surface of the reactor; a washing liquid supply line 400 connected to a first point 410 of the product discharge line 200; and a washing liquid discharge line 500 extending from a second point 510 of the product discharge line 200, wherein the product discharge line 200 includes a branch point 210 at which the product discharge line 200 is branched into two or more lines and a junction point 220 at which the respective branched lines are joined, and the product discharge line includes pressure control devices 300 provided in each of the two or more branched lines.

According to an exemplary embodiment of the present invention, the reactor 100 can be for preparing an oligomer by oligomerizing monomers in the presence of a catalyst and a solvent.

According to an exemplary embodiment of the present invention, the reactor 100 can be a reactor 100 suitable for a continuous process. For example, the reactor 100 can include one or more reactors selected from the group consisting of a continuous stirred-tank reactor, a plug flow reactor, and a bubble column reactor. Therefore, it is possible to continuously prepare oligomeric products.

According to an exemplary embodiment of the present invention, the monomer can include ethylene. Specifically, a monomer stream including ethylene monomers is supplied to reactor 100 and is subjected to an oligomerization reaction, such that a desired alpha-olefin product can be prepared. In this case, the oligomerization reaction is performed in a lower area to a central area of the reactor 100, and the oligomerization reaction of the monomers can be performed in a liquid state in which the monomers are dissolved in a solvent in the presence of a catalyst and a cocatalyst. The oligomerization reaction can refer to a reaction in which the monomers are oligomerized. Depending on the number of monomers that are oligomerized, the oligomerization reaction is called trimerization or tetramerization, and is collectively called multimerization.

The alpha-olefins are an important material used in comonomers, detergents, lubricants, plasticizers, and the like, and are commercially widely used. Among them, 1-hexene and 1-octene are widely used as comonomers for controlling a density of polyethylene at the time of preparing linear low-density polyethylene (LLDPE). The alpha-olefins such as 1-hexene and 1-octene can be prepared through, for example, a trimerization reaction or a tetramerization reaction of ethylene According to an exemplary embodiment of the present invention, the oligomerization reaction of the monomer can be performed as a homogeneous liquid phase reaction, a slurry reaction in which a catalyst is not partially dissolved or is not completely dissolved, a two-phase liquid/liquid reaction, or a bulk phase reaction or a gas phase reaction in which a product acts as a main medium, in the presence or absence of a solvent by applying a reaction system and a general contact technology.

The catalyst can include a transition metal source. The transition metal source can be, for example, a compound including one or more selected from the group consisting of chromium (III) acetylacetonate, chromium (III) chloride tetrahydrofuran, chromium (III) 2-ethylhexanoate, chromium (III) tris(2,2,6,6)-tetramethyl-3,5-heptanedionate), chromium (III) benzoylacetonate, chromium (III) hexafluoro-2,4-pentanedionate, chromium (III) acetatehydroxide, chromium (III) acetate, chromium (III) butyrate, chromium (III) pentanoate, chromium (III) laurate, and chromium (III) stearate.

The cocatalyst can include, for example, one or more selected from the group consisting of trimethyl aluminum, triethyl aluminum, triisopropyl aluminum, triisobutyl aluminum, ethylaluminum sesquichloride, diethylaluminum chloride, ethyl aluminum dichloride, methylaluminoxane, modified methylaluminoxane, and borate.

In a process of oligomerizing the monomers in the presence of the catalyst and the solvent as such, by-products such as wax and polymer are generated in addition to the oligomer product. In a case where these by-products are discharged through a pipe together with the oligomer product, there is a problem that these by-products are attached to an inner wall of a pipe and an inner portion of a valve due to adhesiveness of the polymer to plug the pipe and the valve.

On the other hand, in the present invention, the branch point 210 at which the product discharge line 200 is branched into two or more lines and the junction point 220 at which the respective branched lines are joined are formed in the product discharge line 200 through which the product is discharged from the reactor 100, and the pressure control devices 300 are provided in each of the branched lines to prevent precipitation of the polymer in a product discharge stream, such that a plugging phenomenon of the product discharge line 200 can be prevented, and the respective branched lines are alternately used, such that an operation cycle can be extended. In addition, the apparatus for preparing an oligomer can include the washing liquid supply line 400 and the washing liquid discharge line 500 to easily wash fouling at inlets of the pressure control devices 300 formed in the respective branched lines and wash pipes and the pressure control devices 300 formed in the respective branched lines without stopping an operation of the reactor 100.

According to an exemplary embodiment of the present invention, the reactor 100 can be supplied with the monomer stream and the solvent stream to perform the oligomerization reaction.

The monomer stream can be supplied to the reactor 100 through a monomer stream supply line provided below the reactor 100. In this case, the monomers can be supplied to the reactor 100 in a gas phase. Specifically, the monomer stream including the gas-phase monomers can be supplied to the reactor 100, and the gas-phase monomers can be dissolved in the solvent supplied to the reactor 100 to be subjected to the oligomerization reaction in a liquid phase.

The monomer stream can be supplied from a naphtha cracking center (NCC). The naphtha cracking center can include a step of injecting naphtha, C2 and C3 hydrocarbon compounds, propane, and the like, as feedstock, and performing cracking in each cracking furnace; a step of cooling a cracked gas generated by the cracking in each cracking furnace and including hydrogen, C1, C2 and C3 or more hydrocarbon compounds; a step of compressing the cooled cracked gas; and a step of purifying the cracked compressed stream including hydrogen, C1, C2 and C3 or more hydrocarbon compounds. In this case, the monomer stream can be a stream including ethylene (C2) separated from naphtha cracking.

The solvent stream can be supplied to the reactor 100 through a solvent stream supply line provided on a lower portion of a side surface of the reactor 100. The solvent can include one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene and trichlorobenzene. In some cases, a mixture of two or more of those described above can be used as the solvent. Therefore, the gas-phase ethylene monomers can be liquefied at a higher temperature, and a dissolution rate at which the gas-phase ethylene monomers are dissolved in the solvent can be improved.

According to an exemplary embodiment of the present invention, the apparatus for preparing an oligomer can further include an unreacted monomer discharge line for discharging a stream including unreacted monomers that are not dissolved in the solvent and do not participate in the oligomerization reaction, the unreacted monomer discharge line being provided above the reactor 100. The stream including the unreacted monomers can be in a gas phase. The unreacted monomers can be later separated and recovered from the stream including the gas-phase unreacted monomers discharged through the unreacted monomer discharge line and be re-supplied to the reactor 100 to be reused for the oligomerization reaction.

The oligomerization reaction performed by supplying the monomer stream and the solvent stream to the reactor 100 can be performed at a temperature of 10° C. to 180° C., 30° C. to 150° C., or 50° C. to 120° C. In addition, the oligomerization reaction can be performed at a pressure of 10 to 70 bar. For example, the oligomerization reaction can be performed at a pressure of 10 to 70 bar, 20 to 65 bar, or 30 to 60 bar. When the ethylene is oligomerized within the temperature range and the pressure range described above, selectivity to a desired alpha-olefin may be excellent, an amount of by-products may be decreased, operational efficiency of a continuous process may be increased, and a cost may be decreased.

A liquid-phase stream including the oligomer product through the oligomerization reaction can be discharged through the product discharge line 200 provided on the lower portion of the side surface of the reactor 100, for example, provided to be opposite to and spaced apart from the lower portion of the side surface of the reactor 100 on which the solvent supply line is formed. For example, the product discharge line 200 can be formed at the same height as the solvent supply line. In addition, the product discharge line 200 can be connected to a subsequent process such as a separate storage tank or a purifying portion to transfer the product discharge stream discharged from the reactor 100 to a subsequent process.

In order to keep a catalytic reaction in the reactor 100 constant, a liquid level of the liquid phase should be controlled. To this end, a liquid level control valve can be formed in an area of the product discharge line 200 adjacent to the reactor 100. A pressure of a high-pressure product discharge stream discharged to the product discharge line 200 is decreased while the high-pressure product discharge stream is passing through the liquid level control valve. In this case, a polymer material having high adhesiveness is precipitated while a gas phase and a liquid phase are being separated from each other, such that plugging may occur in the pipe. On the other hand, in the present invention, the pressure control devices 300 are provided to maintain a pressure of the product discharge stream at a level similar to an operation pressure of the reactor 100, thereby solving the problem described above.

The product discharge line 200 can include the branch point 210 at which the product discharge line is branched into two or more lines and the junction point 220 at which the respective branched lines are joined. Specifically, the product discharge line 200 can be branched into two or more lines after the branch point 210, and the respective branched lines can be joined as one line at the junction point 220. For example, the product discharge line 200 can be branched into n lines after the branch point 210. In this case, n can be 2 to 5, 2 to 3, or 2. As a specific example, the product discharge line 200 can be branched into two lines, that is, a first line L1 and a second line L2 after the branch point 210, and the branched first line L1 and second line L2 can be joined as one line at the junction point 220. In this case, in the product discharge line 200, the branch point 210 can be formed in an area more adjacent to the reactor 100 than an area of the junction point 220.

The pressure control devices 300 can be provided in each of the two or more branched lines between the branch point 210 and the junction point. The pressure control device 300 can include, for example, a back pressure regulator (BPR) and a pressure control valve.

The pressure control device 300 can control a pressure of the stream supplied to the pressure control device 300 or control a pressure of the stream discharged from the pressure control device 300. As a specific example, the pressure control device 300 controls the pressure of the stream supplied to the pressure control device 300, and can use the back pressure regulator. In this case, the pressure control device 300 can be installed in an area adjacent to a subsequent process.

The pressure control device 300 can maintain the pressure of the product discharge stream discharged from the reactor 100 at a level similar to the operation pressure of the reactor 100. For example, the pressure of the product discharge stream passing through the pressure control device 300 can be maintained to have a difference of 0 to 10 bar, 0 to 5 bar, or 1 to 3 bar from the operation pressure of the reactor 100. Specifically, in transferring the product discharge stream to the subsequent process using the pressure control device 300, it can be prevented that the polymer material having the high adhesiveness is precipitated while the separation between the gas phase and the liquid phase is occurring due to the decrease in the pressure of the high-pressure product discharge stream generated when the high-pressure product discharge stream passes through the liquid level control valve.

In the product discharge line 200, when any one of the two or more branched lines is opened, the other of the two or more branched lines can be closed. For example, in a case where the product discharge line 200 is branched into the first line and the second line at the branch point 210 and the respective branched lines are joined at the junction point 220, when the first line is opened, the second line can be closed, and when the first line is closed, the second line can be opened. As described above, by branching the product discharge line 200 into a plurality of lines and alternately using the branched lines, an operation stop cycle for washing the fouling of the pressure control device 300 can be extended.

According to an exemplary embodiment of the present invention, in the product discharge line 200, washing pipes for washing the fouling of the pressure control devices 300 provided in each of the plurality of lines formed between the branch point 210 and the junction point 220 can be provided. Specifically, the washing liquid supply line 400 for supplying a washing liquid to the product discharge line 200 and a washing liquid discharge line 500 can be provided. The washing liquid supply line 400 and the washing liquid discharge line 500 are provided, such that the pipes and the fouling of the pressure control devices 300 can be washed by a method of washing any one or more of the two or more branched lines using the washing liquid supplied to the washing liquid supply line and discharging the washing liquid through the washing liquid discharge line.

Specifically, the washing liquid supply line 400 can be provided to be connected to the first point 410 of the product discharge line 200, and the washing liquid discharge line 500 can be provided to extend from the second point 510 of the product discharge line 200.

Figure 1:
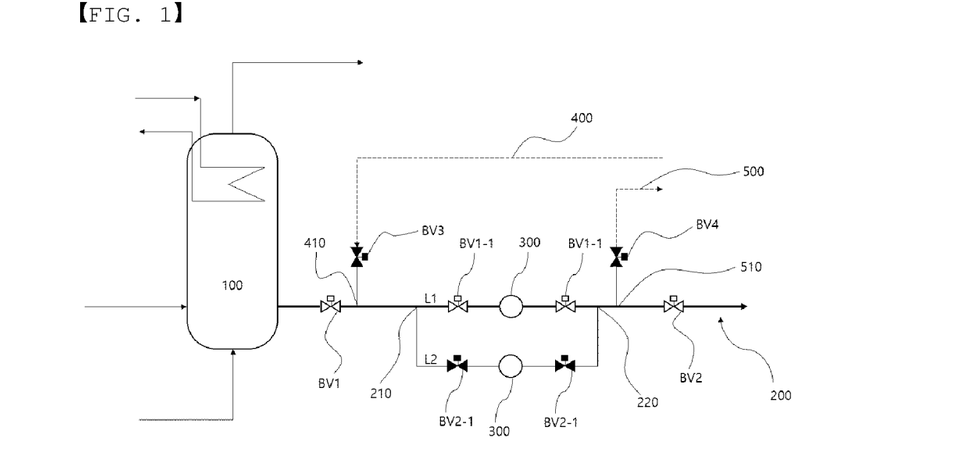
FIG. 1 is a process flow diagram of an apparatus for preparing an oligomer according to an exemplary embodiment of the present invention.
Figure 2:
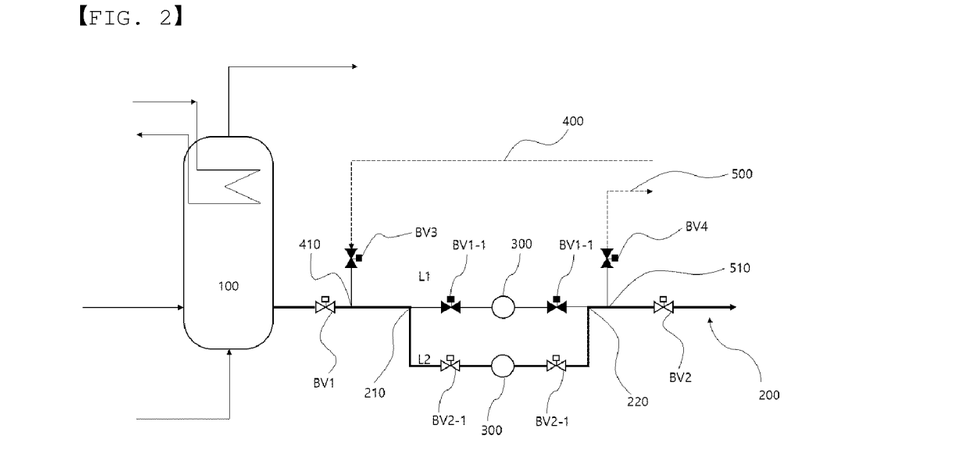
FIG. 2 is a process flow diagram of the apparatus for preparing an oligomer according to an exemplary embodiment of the present invention.
Figure 3:
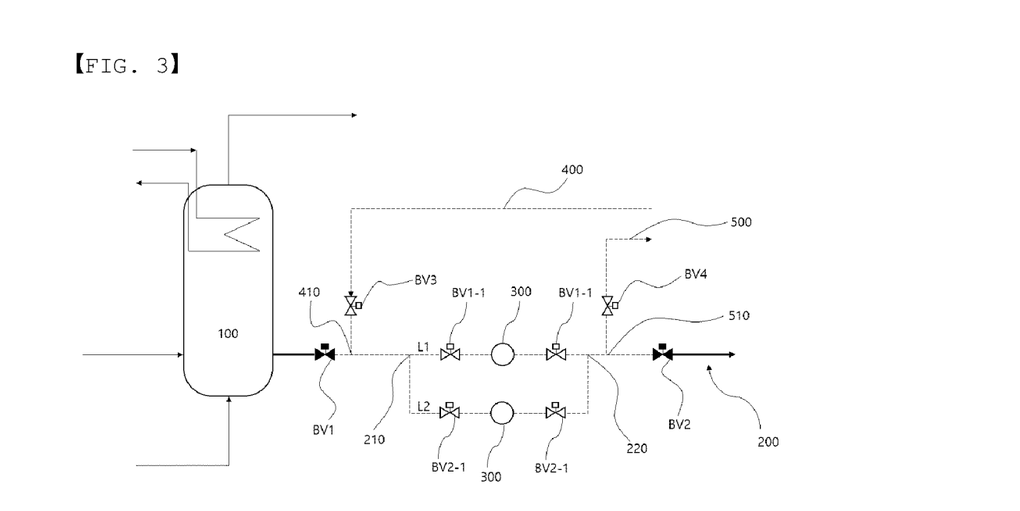
FIG. 3 is a process flow diagram for washing the apparatus for preparing an oligomer according to an exemplary embodiment of the present invention.

As an example, as illustrated in FIGS. 1 to 3, in the product discharge line 200, the first point 410 can be formed in an area more adjacent to the reactor 100 than an area of the branch point 210. Specifically, when the washing liquid is supplied to the product discharge line 200 through the first point 410, the washing liquid is supplied to the area more adjacent to the reactor 100 than the area of the branch point 210, such that the washing liquid can be supplied in a direction from the inlets of the pressure control devices 300 to outlets of the pressure control devices 300, and thus, the fouling of the inlets of the pressure control devices 300 can be easily washed together with the pipes.

In this case, in the product discharge line 200, the second point 510 can be formed in an area more distant from the reactor 100 than an area of the junction point 220. Therefore, the washing liquid that has washed the pipes and the pressure control devices 300 between the first point 410 and the second point 510 can be easily discharged.

Positions at which the first point 410, the second point 510 and valves are formed can be controlled in order to wash the product discharge line 200 as described above. Specifically, the product discharge line 200 includes a first shut-off valve BV1 formed in an area more adjacent to the reactor 100 than an area of the first point 410 and a second shut-off valve BV2 formed in an area more distant from the reactor than an area of the second point 510, the washing liquid supply line 400 includes a third shut-off valve BV3 formed in an arbitrary area, the washing liquid discharge line 500 can include a fourth shut-off valve BV4 formed in an arbitrary area, and the product discharge line 200 can be washed by controlling these valves.

For example, as illustrated in FIG. 1 or FIG. 2, at the time of an operation of the reactor 100, the first shut-off valve BV1 and the second shut-off valve BV2 can be opened to transfer the product discharge stream (bold solid line) discharged from the reactor 100 through the product discharge line 200, and the third shut-off valve BV3 and the fourth shut-off valve BV4 can be closed to prevent inflow of the washing liquid (dotted line) from the washing liquid supply line 400 and the washing liquid discharge line 500 or outflow of the product discharge stream into the washing liquid supply line 400 and the washing liquid discharge line 500.

In addition, shut-off valves can be further provided on both sides of the pressure control devices 300 provided in the respective branched lines of the product discharge line 200. The shut-off valves provided on both sides of the pressure control devices 300 can be opened or closed in the same manner for each line. For example, at the time of the operation of the reactor 100, in order to transfer the product through the product discharge line 200, as illustrated in FIG. 1, the shut-off valves provided on both sides of the pressure control device 300 of the first line L1 branched from the product discharge line 200 can be opened and the shut-off valves provided on both sides of the pressure control device 300 of the other line, that is, the second line L2 can be closed to select the first line L1 and transfer the product discharge stream (bold solid line). In addition, as illustrated in FIG. 2, the shut-off valves provided on both sides of the pressure control device 300 of the second line L2 branched from the product discharge line 200 can be opened and the shut-off valves provided on both sides of the pressure control device 300 of the other line, that is, the first line L1 can be closed to select the second line L2 and transfer the product discharge stream (bold solid line).

In addition, when the product discharge stream of the reactor 100 is closed and the product discharge line 200 is washed, the first shut-off valve BV1 and the second shut-off valve BV2 are closed to closed the transfer of the product discharge stream (bold solid line) discharged from the reactor 100, and the third shut-off valve BV3 and the fourth shut-off valve BV4 are opened to supply the washing liquid (dotted line), thereby making it possible to wash the pipes and the pressure control devices 300 of the product discharge line 200 between the first shut-off valve BV1 and the second shut-off valve BV2. Specifically, as illustrated in FIG. 3, the product discharge stream of the reactor 100 can be closed and the shut-off valves provided on both sides of the pressure control devices 300 of both the first line L1 and the second line L2 of the product discharge line 200 can be opened to wash both lines at once.

Figure 4:
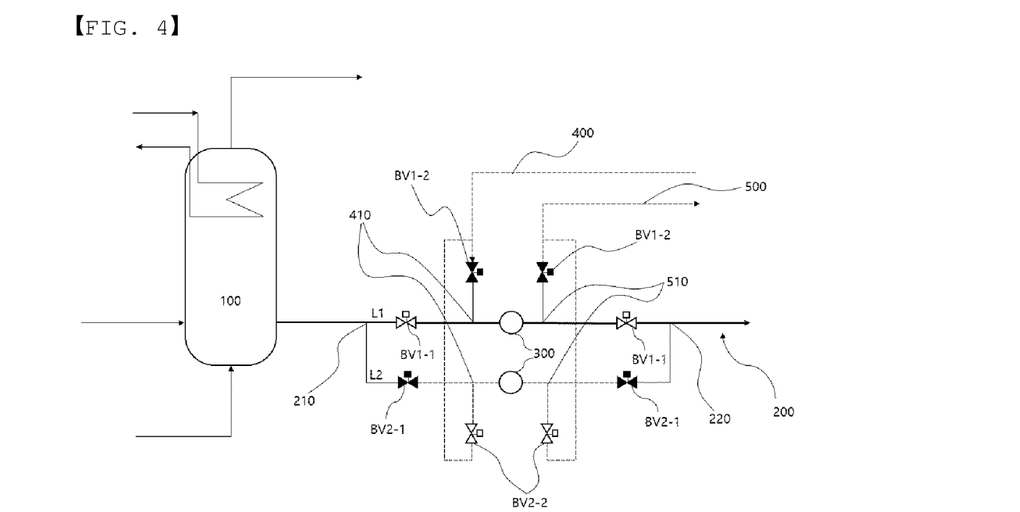
FIG. 4 is a process flow diagram of the apparatus for preparing an oligomer that simultaneously performs preparing of an oligomer and washing of a pressure control device according to an exemplary embodiment of the present invention.
Figure 5:
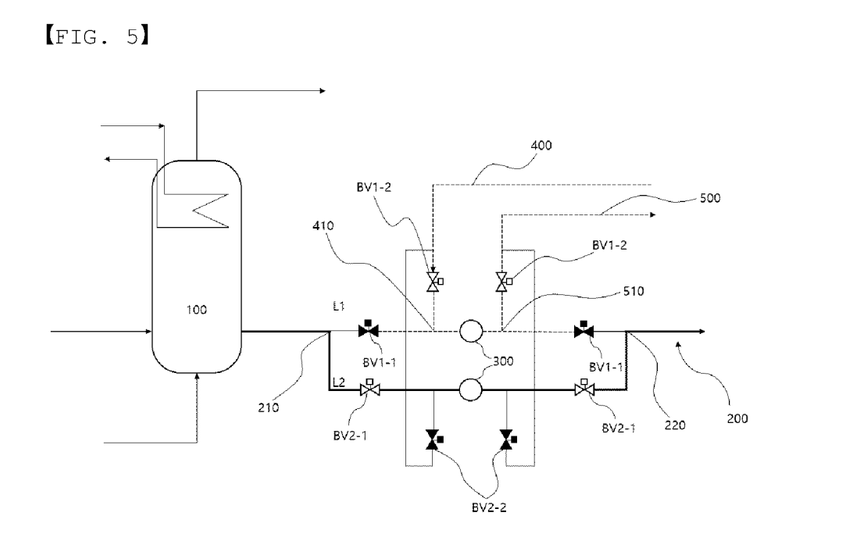
FIG. 5 is process flow diagram of the apparatus for preparing an oligomer that simultaneously performs preparing of an oligomer and washing of a pressure control device according to an exemplary embodiment of the present invention.

As another example, as illustrated in FIGS. 4 and 5, in the product discharge line 200, each of the first points 410 and the second points 510 can be formed in each of the two or more branched lines. Specifically, each of the first points 410 and the second points 510 are formed in each of the two or more branched lines, such that the two or more lines branched between the branching point 210 and the junction point 220 can be individually washed. More specifically, when the product discharge stream is transferred through any one of the two or more branched lines, the other of the two or more branched lines can be washed.

In addition, the first points 410 can be formed in areas between the branch point 210 and points at which the pressure control devices 300 are provided. Specifically, the first points 410 to which the washing liquid is supplied are formed in the areas between the branch point 210 and the points at which the pressure control devices 300 are provided, such that the washing liquid can be supplied in the direction from the inlets of the pressure control device 300 to the outlets of the pressure control devices 300, and thus, the fouling of the inlets of the pressure control devices 300 can be easily washed together with the pipes.

In this case, the second points 510 can be formed in areas between the points at which the pressure control devices 300 are provided and the junction point 220. Therefore, the washing liquid that has washed any one of the two or more branched lines and the pressure control device 300 provided in such a line can be easily discharged.

As described above, the positions at which the first points 410, the second points 510 and valves are formed can be controlled in order to wash the product discharge line 200 as described above. Specifically, in each of the two or more branched lines of the product discharge line 200, n–1-th shut-off valves each formed on both sides of the pressure control device 300 can be included. Two n–1-th shut-off valves can be installed, for example, at a front end and a rear end of the pressure control device 300. In this case, the front end can refer to an area adjacent to the reactor 100 with respect to the pressure control device 300, and the rear end can refer to an area distant from the reactor 100 with respect to the pressure control device 300. In addition, the first point 410 and the second point 510 can be formed between the respective n–1-th shut-off valves and the pressure control device 300, respectively. In this case, the first point 410 can be formed between the pressure control device 300 and the n–1-th shut-off valve installed at the front end of the pressure control device 300, and the second point 510 can be formed between the pressure control device 300 and the n–1-th shut-off valve installed at the rear end of the pressure control device 300. In addition, n–2-th shut-off valves formed in arbitrary areas of the washing liquid supply line 400 and the washing liquid discharge line 500 connected to the respective first points 410 and second points 510 can be included, and the product discharge line 200 can be washed by controlling these valves.

In this case, the two or more branched lines of the product discharge line 200 can be individually operated or washed, and thus, the reactor 100 can be alternately operated in n modes, such that it is possible to continuously operate the reactor 100 without stopping the operation of the reactor 100. Specifically, when the reactor 100 is operated in an n-th mode, in a case where the n–1-th shut-off valves of an n-th line are opened in each of the two or more branched lines, the n–2-th shut-off valves formed in the arbitrary areas of each of the washing liquid supply line 400 and the washing liquid discharge line 500 connected to the first point 410 and the second point 510 of the line in which the n–1-th shut-off valves are opened can be closed. In addition, the n–1-th shut-off valves of the other line can be closed, and the n–2-th shut-off valves formed in the arbitrary areas of the washing liquid supply line 400 and the washing liquid discharge line 500 connected to the first point 410 and the second point 510 of the line in which the n–1-th shut-off valves are closed can be opened. In this case, the n-th line may refer to any one of two to five branched lines, two or three branched lines, or two branched lines.

More specifically, a case where the product discharge line 200 is branched into the first line L1 and the second line L2 at the branch point 210 will be described by way of example. The reactor 100 can be alternately operated in a first mode or a second mode.

As illustrated in FIG. 4, when the reactor 100 is operated in the first mode, 1-1-th shut-off valves BV1-1 each formed on both sides of the pressure control device 300 provided in the first line L1 can be opened to transfer the product discharge stream (bold solid line) discharged from the reactor 100 using the first line L1. In this case, 1-2-th shut-off valves BV1-2 formed in the arbitrary areas of each of the washing liquid supply line 400 and the washing liquid discharge line 500 connected to the first point 410 and the second point 510 of the first line L1 can be closed to prevent the washing liquid from the washing liquid supply line 400 and the washing liquid discharge line 500 from flowing into the first line L1 or the product discharge stream of the first line L1 from flowing out to the washing liquid supply line 400 and the washing liquid discharge line 500. At the same time, 2-1-th shut-off valves BV2-1 formed on both sides of the pressure control device 300 provided in the other line, that is, the second line L2 can be closed to closed the transfer of the product discharge stream discharged from the reactor 100 to the second line L2. In addition, 2-2-th shut-off valves BV2-2 formed in the arbitrary areas of each of the washing liquid supply line 400 and the washing liquid discharge line 500 connected to the first point 410 and the second point 510 of the second line L2 can be opened to selectively wash the second line L2 while circulating the washing liquid (dotted line) in the second line L2.

In addition, as illustrated in FIG. 5, when the reactor 100 is operated in the second mode, the 2-1-th shut-off valves BV2-1 each formed on both sides of the pressure control device 300 provided in the second line L2 can be opened to transfer the product discharge stream (bold solid line) discharged from the reactor 100 using the second line L2. In this case, the 2-2-th shut-off valves BV2-2 formed in the arbitrary areas of each of the washing liquid supply line 400 and the washing liquid discharge line 500 connected to the first point 410 and the second point 510 of the second line L2 can be closed to prevent the washing liquid from the washing liquid supply line 400 and the washing liquid discharge line 500 from flowing into the second line L2 or the product discharge stream of the second line L2 from flowing out to the washing liquid supply line 400 and the washing liquid discharge line 500. At the same time, the 1-1-th shut-off valves BV1-1 formed on both sides of the pressure control device 300 provided in the other line, that is, the first line L1 can be closed to closed the transfer of the product discharge stream discharged from the reactor 100 to the first line L1. In addition, the 1-2-th shut-off valves BV1-2 formed in the arbitrary areas of each of the washing liquid supply line 400 and the washing liquid discharge line 500 connected to the first point 410 and the second point 510 of the first line L1 can be opened to selectively wash the first line L1 while circulating the washing liquid (dotted line) in the first line L1.

The reactor 100 can be alternately operated in the first mode and the second mode at a cycle of 0.1 to 12 hours. For example, the reactor 100 can be alternately operated in the first mode and the second mode at a cycle of 0.1 to 12 hours, 0.5 to 6 hours, or 1 to 4 hours. Therefore, it is possible to prevent the inlet of the pressure control device 300 from being plugged due to the polymer material included in the product discharge stream discharged from the reactor 100 and having the adhesiveness.

Specifically, in a case where the reactor 100 is operated in the first mode, the product discharge stream is transferred through the first line L1 and the second line L2 is washed. In this case, when the reactor 100 is operated for about 12 to 72 hours, polymer materials may be accumulated at the inlet of the pressure control device 300 of the first line L1. In this case, an operation mode of the reactor 100 is switched from the first mode to the second mode, such that the first line L1 is washed and the product discharge stream is transferred through the second line L2, thereby making it possible to continuously operate the reactor 100 without stopping the operation of the reactor 100.

According to an exemplary embodiment of the present invention, the apparatus for preparing an oligomer can further include a cooling pipe (not illustrated) for controlling an oligomerization reaction temperature in the reactor 100. A coolant can be supplied to the cooling pipe (not illustrated). Therefore, a part of heat generated in the oligomerization reaction can be removed so that the oligomerization reaction of a reactant performed in the reactor 100 can be performed at a predetermined temperature, and amounts of a liquid-phase low boiling point olefin and a solvent entrained with the unreacted monomers and discharged together with the stream including the unreacted monomers can be decreased.

According to an exemplary embodiment of the present invention, the apparatus for preparing an oligomer can further include additional devices necessary for preparing the oligomer, such as a valve, a condenser, a reboiler, a pump, a separation device, a compressor, and a mixer, if necessary.

The apparatus for preparing an oligomer according to the present invention has been described hereinabove and illustrated in the drawings, but only essential components for understanding the present invention have been described above and illustrated in the drawings, and in addition to the processes and the devices described above and illustrated in the drawings, processes and devices that are not separately described and illustrated may be appropriately applied and used to implement the apparatus for preparing an oligomer according to the present invention.

Hereinafter, the present invention will be described in more detail through Examples. However, the following Examples are provided in order to exemplify the present invention, it is apparent to those skilled in the art that various modifications and alterations may be made without departing from the scope and spirit of the present invention, and the scope of the present invention is not limited to these Examples.

EXAMPLES

Example 1

The apparatus for preparing an oligomer was operated as illustrated in the process flow diagram of FIG. 1.

Specifically, the alpha-olefin was prepared by supplying the gas-phase ethylene monomer stream to the lower portion of the reactor 100 and supplying the solvent stream to the lower portion of the side surface of the reactor 100 to oligomerize the ethylene monomers.

In this case, in transferring the product discharge stream (bold solid line) discharged from the reactor 100 through the product discharge line 200 by opening the first shut-off valve BV1 and the second shut-off valve BV2, the third shut-off valve BV3 and the fourth shut-off valve BV4 were closed to closed the supply of the washing liquid (dotted line) to the product discharge line 200.

In addition, the shut-off valves each provided on both sides of the pressure control device 300 of the first line L1 branched from the product discharge line 200 were opened, and the shut-off valves each provided on both sides of the pressure control device 300 of the second line L2 were closed to select the first line L1 and transfer the product discharge stream (bold solid line).

Example 2

The apparatus for preparing an oligomer was operated as illustrated in the process flow diagram of FIG. 2.

Specifically, the alpha-olefin was prepared by supplying the gas-phase ethylene monomer stream to the lower portion of the reactor 100 and supplying the solvent stream to the lower portion of the side surface of the reactor 100 to oligomerize the ethylene monomers.

In this case, in transferring the product discharge stream (bold solid line) discharged from the reactor 100 through the product discharge line 200 by opening the first shut-off valve BV1 and the second shut-off valve BV2, the third shut-off valve BV3 and the fourth shut-off valve BV4 were closed to closed the supply of the washing liquid (dotted line) to the product discharge line 200.

In addition, the shut-off valves each provided on both sides of the pressure control device 300 of the second line L2 branched from the product discharge line 200 were opened, and the shut-off valves each provided on both sides of the pressure control device 300 of the first line L1 were closed to select the second line L2 and transfer the product discharge stream (bold solid line).

Example 3

The apparatus for preparing an oligomer was washed as illustrated in the process flow diagram of FIG. 3.

Specifically, the alpha-olefin was prepared by supplying the gas-phase ethylene monomer stream to the lower portion of the reactor 100 and supplying the solvent stream to the lower portion of the side surface of the reactor 100 to oligomerize the ethylene monomers.

In this case, the first shut-off valve BV1 and the second shut-off valve BV2 were closed to closed the transfer of the product discharge stream (bold solid line) discharged from the reactor 100, and the third shut-off valve BV3 and the fourth shut-off valve BV4 were opened to supply the washing liquid (dotted line), thereby washing the pipes and the pressure control devices 300 of the product discharge line 200 between the first shut-off valve BV1 and the second shut-off valve BV2. In this case, the shut-off valves provided on both sides of the pressure control devices 300 of both the first line L1 and the second line L2 of the product discharge line 200 were opened to wash both lines at once.

Example 4

The apparatus for preparing an oligomer was operated in the first mode as illustrated in the process flow diagram of FIG. 4.

Specifically, the alpha-olefin was prepared by supplying the gas-phase ethylene monomer stream to the lower portion of the reactor 100 and supplying the solvent stream to the lower portion of the side surface of the reactor 100 to oligomerize the ethylene monomers.

In this case, when the reactor 100 is operated in the first mode, the 1-1-th shut-off valves BV1-1 each formed on both sides of the pressure control device 300 provided in the first line L1 were opened to transfer the product discharge stream (bold solid line) discharged from the reactor 100 using the first line L1. In this case, the 1-2-th shut-off valves BV1-2 formed in the arbitrary areas of each of the washing liquid supply line 400 and the washing liquid discharge line 500 connected to the first point 410 and the second point 510 of the first line L1 were closed to prevent the washing liquid from the washing liquid supply line 400 and the washing liquid discharge line 500 from flowing into the first line L1 or the product discharge stream of the first line L1 from flowing out to the washing liquid supply line 400 and the washing liquid discharge line 500. At the same time, the 2-1-th shut-off valves BV2-1 formed on both sides of the pressure control device 300 provided in the second line L2 were closed to closed the transfer of the product discharge stream discharged from the reactor 100 to the second line L2. In addition, the 2-2-th shut-off valves BV2-2 formed in the arbitrary areas of each of the washing liquid supply line 400 and the washing liquid discharge line 500 connected to the first point 410 and the second point 510 of the second line L2 were opened to selectively wash the second line L2 while circulating the washing liquid (dotted line) in the second line L2.

Example 5

The apparatus for preparing an oligomer was operated in the second mode as illustrated in the process flow diagram of FIG. 5.

Specifically, the alpha-olefin was prepared by supplying the gas-phase ethylene monomer stream to the lower portion of the reactor 100 and supplying the solvent stream to the lower portion of the side surface of the reactor 100 to oligomerize the ethylene monomers.

In this case, when the reactor 100 is operated in the second mode, the 2-1-th shut-off valves BV2-1 each formed on both sides of the pressure control device 300 provided in the second line L2 were opened to transfer the product discharge stream (bold solid line) discharged from the reactor 100 using the second line L2. In this case, the 2-2-th shut-off valves BV2-2 formed in the arbitrary areas of each of the washing liquid supply line 400 and the washing liquid discharge line 500 connected to the first point 410 and second point 510 of the second line L2 were closed to prevent the washing liquid from the washing liquid supply line 400 and the washing liquid discharge line 500 from flowing into the second line L2 or the product discharge stream of the second line L2 from flowing out to the washing liquid supply line 400 and the washing liquid discharge line 500. At the same time, the 1-1-th shut-off valves BV1-1 formed on both sides of the pressure control device 300 provided in the first line L1 were closed to closed the transfer of the product discharge stream discharged from the reactor 100 to the first line L1. In addition, the 1-2-th shut-off valves BV1-2 formed in the arbitrary areas of each of the washing liquid supply line 400 and the washing liquid discharge line 500 connected to the first point 410 and the second point 510 of the first line L1 were opened to selectively wash the first line L1 while circulating the washing liquid (dotted line) in the first line L1.

COMPARATIVE EXAMPLE

Comparative Example 1

Figure 6:
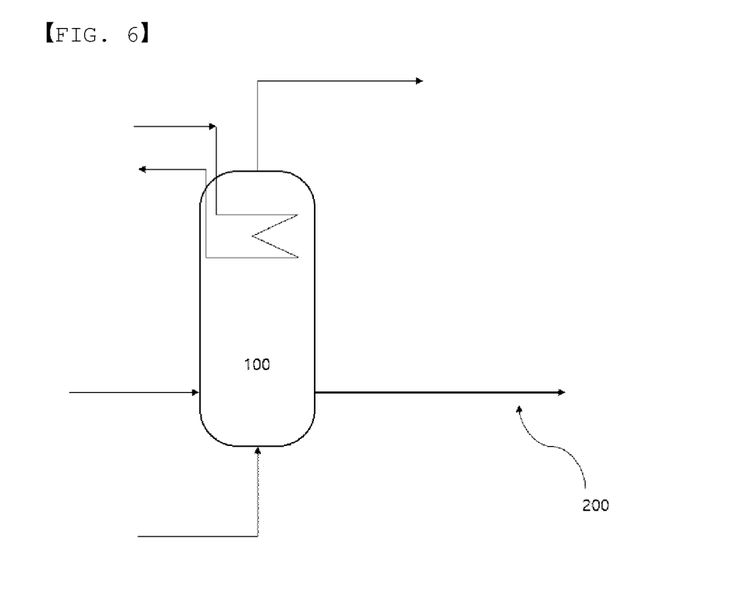
FIG. 6 is a process flow diagram of an apparatus for preparing an oligomer according to a comparative example.

The apparatus for preparing an oligomer was operated as illustrated in the process flow diagram of FIG. 6. Specifically, the alpha-olefin was prepared by supplying the gas-phase ethylene monomer stream to the lower portion of the reactor 100 and supplying the solvent stream to the lower portion of the side surface of the reactor 100 to oligomerize the ethylene monomers.

In this case, the product discharge stream (bold solid line) discharged from the reactor 100 was discharged through the product discharge line 200.

In this case, the high-pressure product discharge stream is discharged through the product discharge line 200, the pressure of the product discharge stream is decreased while the product discharge stream is passing through the liquid level control valve, and there was a problem that the gas phase and the liquid phase are separated from each other due to a pressure drop while the product discharge stream is being transferred to the subsequent process operated at a pressure lower than that of the reactor. In this case, there was a problem that the fouling occurs in the pipes while the polymer material having the adhesiveness is being precipitated.

The invention claimed is:

1. An apparatus for preparing an oligomer, comprising:
a reactor supplied with a monomer stream and a solvent stream to perform an oligomerization reaction;
a product discharge line provided on a lower portion of a side surface of the reactor;
a washing liquid supply line connected to a first point of the product discharge line; and
a washing liquid discharge line extending from a second point of the product discharge line,
wherein the product discharge line includes a branch point at which the product discharge line is branched into two or more lines and a junction point at which the respective branched lines are joined, and
wherein the product discharge line includes pressure control devices provided in each of the two or more branched lines.

2. The apparatus for preparing an oligomer of claim 1, wherein in the product discharge line, the branch point is formed in an area more adjacent to the reactor than an area of the junction point.

3. The apparatus for preparing an oligomer of claim 1, wherein the product discharge line is branched into n lines at the branch point, and wherein (n is 2 to 5).

4. The apparatus for preparing an oligomer of claim 1, wherein when any one of the two or more branched lines is opened, the other of the two or more branched lines is closed.

5. The apparatus for preparing an oligomer of claim 1, wherein the product discharge line is branched from the branch point into a first line and a second line, and the first and second branched lines are joined as one line at the junction point.

6. The apparatus for preparing an oligomer of claim 1, wherein a pressure of a stream passing through the pressure control device is maintained to have a difference of 0 to 10 bar from an operation pressure of the reactor.

7. The apparatus for preparing an oligomer of claim 1, wherein at least one of the two or more branched lines is washed using a washing liquid supplied to the washing liquid supply line, and the washing liquid is discharged through the washing liquid discharge line.

8. The apparatus for preparing an oligomer of claim 1, wherein in the product discharge line, the first point is formed in an area more adjacent to the reactor than an area of the branch point, and the second point is formed in an area more distant from the reactor than an area of the junction point.

9. The apparatus for preparing an oligomer of claim 8, wherein, the product discharge line includes a first shut-off valve formed in an area more adjacent to the reactor than the area of the first point and a second shut-off valve formed in an area more distant from the reactor than the area of the second point,
wherein the washing liquid supply line includes a third shut-off valve, and
wherein the washing liquid discharge line includes a fourth shut-off valve.

10. The apparatus for preparing an oligomer of claim 9, wherein, when a product is transferred through the product discharge line, the first shut-off valve and the second shut-off valve are opened, and the third shut-off valve and the fourth shut-off valve are closed, and wherein, when the product discharge line is washed, the first shut-off valve and the second shut-off valve are closed, and the third shut-off valve and the fourth shut-off valve are opened.

11. The apparatus for preparing an oligomer of claim 1, wherein the first points and the second points are formed in each of the two or more branched lines,
   wherein the first points are formed in areas between the branch point and points at which the pressure control devices are provided, and
   wherein the second points are formed in areas between the points at which the pressure control devices are provided and the junction point.

12. The apparatus for preparing an oligomer of claim 11, wherein, in each of the two or more branched lines, n–1-th shut-off valves are formed on both sides of the pressure control device,
   wherein, in each of the two or more branched lines, the first point and the second point are formed between the respective n–1-th shut-off valves and the pressure control device, respectively,
   wherein, in each of the two or more branched lines, n–2-th shut-off valves formed in arbitrary areas of the washing liquid supply line and the washing liquid discharge line connected to the respective first points and second points are included, and
   wherein n is a number between 1 and the number of branched lines.

13. The apparatus for preparing an oligomer of claim 12, wherein the reactor is alternately operated in n modes,
   wherein, when the reactor is operated in an n-th mode, in a case where n–1-th shut-off valves of an n-th branched line are opened in each of the two or more branched lines, n–2-th shut-off valves formed in arbitrary areas of the washing liquid supply line and the washing liquid discharge line connected to the first point and the second point of the line in which the n–1-th shut-off valves are opened are closed, and
   n–1-th shut-off valves of the other branched lines are closed, and n–2-th shut-off valves formed in arbitrary areas of the washing liquid supply line and the washing liquid discharge line connected to the first point and the second point of the line in which the n–1-th shut-off valves are closed are opened.

14. The apparatus for preparing an oligomer of claim 1, wherein the monomer includes ethylene, and the oligomer includes an alpha-olefin.

* * * * *